United States Patent
Chaloin et al.

(10) Patent No.: US 9,783,541 B2
(45) Date of Patent: Oct. 10, 2017

(54) 5'-NUCLEOTIDASE INHIBITORS AND THERAPEUTIC USES THEREOF

(71) Applicants: Centre National de la Recherche Scientifique-CNRS, Paris (FR); Hospices Civils de Lyon, Lyons (FR); Ecole Normale Superieure de Lyon, Lyons (FR); Universite Claude Bernard Lyon 1, Villeurbanne (FR); Universite de Montpellier 1, Montpellier (FR)

(72) Inventors: Laurent Chaloin, Prades le Lez (FR); Suzanne Peyrottes, Grabels (FR); Corinne Lionne, St Gely du Fesc (FR); Zsuzsanna Marton, La Baule-escoublac (FR); David Egron, Grabels (FR); Remi Guillon, Montpellier (FR); Christian Perigaud, Grabels (FR); Charles Dumontet, Venissieux (FR); Lars Petter Jordheim, Saint-priest (FR); Isabelle Krimm, Genay (FR)

(73) Assignees: CENTRE NATIONAL DE LA RECHERCHE SCIENTIFIQUE-CNRS, Paris (FR); HOSPICES CIVILS DE LYON, Lyon (FR); ECOLE NORMALE SUPERIEURE DE LYON, Lyon (FR); UNIVERSITE CLAUDE BERNARD LYON 1, Villeurbanne (FR); UNIVERSITE DE MONTPELLIER 1, Montpellier (FR)

( * ) Notice: Subject to any disclaimer, the term of this patent is extended or adjusted under 35 U.S.C. 154(b) by 5 days.

(21) Appl. No.: 15/023,911

(22) PCT Filed: Sep. 29, 2014

(86) PCT No.: PCT/FR2014/052447
§ 371 (c)(1),
(2) Date: Mar. 22, 2016

(87) PCT Pub. No.: WO2015/049447
PCT Pub. Date: Apr. 9, 2015

(65) Prior Publication Data
US 2016/0272643 A1  Sep. 22, 2016

(30) Foreign Application Priority Data
Oct. 1, 2013 (FR) ...................... 13 59472

(51) Int. Cl.
| | | |
|---|---|---|
| A01N 43/04 | (2006.01) |
| A61K 31/70 | (2006.01) |
| C07D 473/34 | (2006.01) |
| A61K 45/06 | (2006.01) |
| A61K 31/52 | (2006.01) |
| A61K 31/675 | (2006.01) |
| A61K 31/7076 | (2006.01) |
| C07F 9/6561 | (2006.01) |
| A61K 31/7064 | (2006.01) |
| A61K 31/706 | (2006.01) |
| A61K 31/7068 | (2006.01) |
| A61K 31/7072 | (2006.01) |
| A61K 31/708 | (2006.01) |

(52) U.S. Cl.
CPC ............ *C07D 473/34* (2013.01); *A61K 31/52* (2013.01); *A61K 31/675* (2013.01); *A61K 31/7076* (2013.01); *A61K 45/06* (2013.01); *C07F 9/65616* (2013.01); *A61K 31/706* (2013.01); *A61K 31/708* (2013.01); *A61K 31/7064* (2013.01); *A61K 31/7068* (2013.01); *A61K 31/7072* (2013.01)

(58) Field of Classification Search
None
See application file for complete search history.

(56) References Cited

FOREIGN PATENT DOCUMENTS

| WO | 98/05335 | 2/1998 |
| WO | 00/44750 | 8/2000 |

OTHER PUBLICATIONS

Reid et al. Helvetica Chimica Acta (1989), vol. 72, pp. 1597-1607.*
Ried et al.: "Strukturaufklärung von N6-, 9-und 7-Acyladeninen durch 1H-und 13C-NMR-Spektroskopie von Festkörpern und in Lösung", Helvetica Chimica Acta., vol. 72, 1989, pp. 1597-1607, XP002725623, Chverlag Helvetica Chimica Acta, Basel. ISSN: 0018-019X, shema I; p. 1605; compound 3e (Abstract).

* cited by examiner

*Primary Examiner* — Patrick Lewis
(74) *Attorney, Agent, or Firm* — McAndrews, Held & Malloy, Ltd.

(57) ABSTRACT

The subject matter of the present invention is compounds which have a 6-aminopurine backbone corresponding to formula (I): in which $R_1$, $R_2$, $R_3$, X, Y and Z are as defined in any one of claims 1 to 5, and Ar is a biphenyl or a naphthyl which may be substituted with $R_3$, for use in the treatment of cancer.

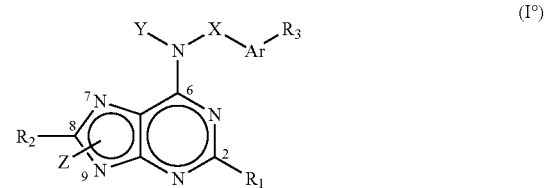

(I°)

14 Claims, 4 Drawing Sheets

(III)

Fig. 2b

(III)

Figure 3

(III)

5'-NUCLEOTIDASE INHIBITORS AND THERAPEUTIC USES THEREOF

The present application is filed pursuant to 35 U.S.C. 371 as a U.S. National Phase application of International Patent Application No. PCT/FR2014/052447, which was filed Sep. 29, 2014, claiming the benefit of priority to French Patent Application No. 1359472, which was filed on Oct. 1, 2013. The entire text of the aforementioned applications is incorporated herein by reference in its entirety.

The present invention relates to novel compounds which have a 6-aminopurine backbone, as 5'-nucleotidase inhibitors, and in particular cytosolic 5'-nucleotidase II (cN-II) inhibitors. The invention also relates to the use of said compounds, alone or in combination with the nucleoside and/or nucleobase analogs, in anticancer chemotherapy.

Nucleoside analogs represent a class of therapeutic agents widely used in the treatment of malignant hemopathies and solid tumors. Their mode of action is based on an intracellular metabolization into their phosphorylated derivatives (nucleotides) which interferes with the enzymatic systems involved in nucleic acid biosynthesis (polymerases, ribonucleotide reductase, thymidylate synthase etc.).

Nucleobase analogs such as 6-mercaptopurine derivatives have thus far been described for the treatment of acute lymphoblastic leukemias, acute myeloblastic leukemias and chronic myeloid leukemias in adults and children. There are not very many orally administered anticancer drugs in pediatrics, but such drugs are frequently used in various cases of malignant pathologies such as leukemias, Hodgkin's disease, non-Hodgkin's lymphomas, brain tumors, etc. Their mode of action is similar to nucleoside analogs.

The use of nucleoside analogs nevertheless comes up against the occurrence of resistance phenomena, involving in particular an enzymatic dysregulation between the intracellular expression of kinases and of 5'-nucleotidases. Thus, the high expression of 5'-nucleotidase activity in diagnosis is known to be an independent predictive factor unfavorable to survival in patients suffering from cancers. By way of example, high expression of cytosolic 5'-nucleotidase II (cN-II) is clinically observed in patients suffering from acute myeloid leukemia having an overall survival which is worse than other patients. Furthermore, recent studies[2a,b] have shown the existence of mutations stimulating the activity of human cN-II leading to increased resistance to treatments with 6-mercaptopurine and 6-thioguanine used in pediatrics.

However, no therapeutic answer has to date been provided to the modulation of nucleotide concentrations resulting from the expression or overexpression of 5'-nucleotidases.

Document US 2010/0204182 describes ectonucleotidase inhibitors for the treatment of diverse and varied diseases such as dry eye disease, respiratory diseases, cystic fibrosis, inflammatory diseases, diseases of the immune system, gastrointestinal diseases, kidney disorders, cancers and brain diseases.

However, the pharmacological target in this document is a membrane target (and not cytosolic) and the intended applications are extremely broad.

The document "Biochem. J. (1989) 262, 203-8" describes cytosolic 5'-nucleotidase inhibitors present in rat liver and heart extracts; these compounds belong to the 5'-deoxy-5'-alkylthionucleoside family, in particular adenosine derivatives and inosine derivatives.

One of the objectives of the present invention is to provide 5'-nucleotidase inhibitor compounds which can in particular be used in the treatment of cancer.

Another objective of the invention is to provide 5'-nucleotidase inhibitor compounds which, when used in combination with cytotoxic nucleoside analogs and/or nucleobase analogs normally used in anticancer chemotherapy, potentiate the therapeutic effect of said cytotoxic nucleoside analogs and/or nucleobase analogs.

A subject of the present invention is thus a compound which has a 6-aminopurine backbone, characterized in that it has the formula:

wherein $R_1$ and $R_2$, which may be identical or different, represent, independently of one another, hydrogen, alkyl, alkenyl, alkynyl, aryl, acyl (—$COR_9$), amino (—$NH_2$), alkylamino (—$NHR_9$), dialkylamino (—$NR_9R'_9$), acylamino (—NH-$COR_9$), diacylamino (—N($COR_9$)($COR'_9$)), trifluoromethyl (—$CF_3$), halogen, hydroxyl (—OH), alkoxy (—$OR_9$), thio (—SH) or thioalkyl (—$SR_9$), with $R_9$ and $R'_9$, which may be identical or different, representing, independently of one another, alkyl, alkenyl, alkynyl or aryl, Z is on either of the positions $N_7$ and $N_9$ of the purine, and represents hydrogen, alkyl, alkenyl, alkynyl, aryl, —$COR_9$, halogen, —$(CH_2)_n$—$OR_5$, —$(CH_2)_{n1}$—O—$(CH_2)_{n2}R_5$, —$(CH_2)_{n'}$—$COOR_5$ or —$(CH_2)_n$—P(=O)($OR_6$)($OR_7$), with:

n, $n_1$ and $n_2$, which may be identical or different, representing, independently of one another, an integer ranging from 1 to 10 and n' an integer ranging from 0 to 10, $R_5$ representing hydrogen, alkyl, alkenyl, alkynyl, aryl or —$COR_9$, $R_6$ and $R_7$, which may be identical or different, representing, independently of one another, hydrogen, alkyl, alkenyl, alkynyl, aryl, —$COR_9$, an organic cation or a metal cation, X represents a divalent radical chosen from C=O, C=S, C=$NR_8$ or $SO_2$, with:

$R_8$ representing hydrogen, alkyl, alkenyl, alkynyl, —OH or —$OR_9$,

Y has the same meaning as $R_5$,

Ar represents a biphenyl which may be substituted with a substituent $R_3$, $R_3$ represents hydrogen, alkyl, alkenyl, alkynyl, aryl, —$NH_2$, —$NHR_9$, —$NR_9R'_9$, —OH, —$OR_9$, aryloxy, benzyloxy (—$OCH_2C_6H_5$); a 5-membered or 6-membered aromatic or nonaromatic heterocycle comprising one or more heteroatoms chosen from N, O or S, said 5-membered or 6-membered heterocycle also possibly being substituted with a substituent $R_4$, with:

$R_4$ representing hydrogen, alkyl, alkenyl, alkynyl, aryl, —$COR_9$, —$(CH_2)_n$—$OR_5$, —$(CH_2)_{n1}$—O—$(CH_2)_{n2}R_5$, —$(CH_2)_{n'}$—$COOR_5$ or —$(CH_2)_n$—P(=O)($OR_6$) ($OR_7$), with $R_5$, $R_6$, $R_7$, n, $n_1$, $n_2$ and n' as previously defined, $R_3$ being bonded to Ar in the ortho, meta or para position, X being bonded to Ar in the ortho, meta or para position, with the exception of the compound 9H-purin-6-yl-[1,1'-biphenyl]-4-carboxamide.

In the present application, the term "alkyl" denotes a linear or branched, hydrocarbon-based radical advantageously having from 1 to 12 carbon atoms, and preferably from 1 to 6 carbon atoms, such as methyl, ethyl, propyl, isopropyl, butyl, tert-butyl, pentyl, neopentyl or n-hexyl.

The term "alkenyl" denotes a linear or branched, hydrocarbon-based radical comprising one or more carbon-carbon double bonds, advantageously having from 2 to 12 carbon atoms, and preferably from 2 to 6 carbon atoms with one or two double bonds.

The term "alkynyl" denotes a linear or branched, hydrocarbon-based radical comprising one or more carbon-carbon triple bonds, advantageously having from 2 to 12 carbon atoms, and preferably from 2 to 6 carbon atoms with one or two triple bonds.

The term "aryl" denotes a monocyclic, bicyclic or tricyclic aromatic hydrocarbon-based system having from 6 to 18 carbon atoms. By way of example, mention may be made of phenyl ($C_6H_5$), benzyl ($C_6H_5CH_2$), phenethyl ($C_6H_5CH_2CH_2$), tolyl ($C_6H_4CH_3$), xylyl ($C_6H_3(CH_3)_2$), benzylidene ($C_6H_5CH=CH$), benzoyl ($C_6H_5CO$), biphenyl (or diphenyl) ($C_{12}H_9$) and naphthyl ($C_{10}H_7$).

This term "aryl" must be differentiated in the present application from the abbreviation "Ar" represented in the general formula above or in formula (I) defined hereinafter, and which denotes specifically, on the one hand, a biphenyl or, on the other hand, a biphenyl or a naphthyl, each possibly being substituted with a substituent $R_3$ with $R_3$ as previously defined.

The alkyls, alkenyls, alkynyls, aryls as defined in the application can also be substituted with one or more substituents chosen from alkyl, alkenyl, alkynyl, aryl, —$NH_2$, —$NHR_9$, —$NR_9R'_9$, —OH, —$OR_9$, aryloxy, benzyloxy (—$OCH_2C_6H_5$), and a 5-membered or 6-membered aromatic or nonaromatic heterocycle comprising one or more heteroatoms chosen from N, O or S.

The term "halogen" denotes a fluorine, chlorine, iodine or bromine atom.

By way of example of an organic cation, mention may be made of an ammonium, trialkylammonium or pyridinium cation. By way of example of a metal cation, mention may be made of a sodium ($Na^+$), lithium ($Li^+$) or potassium ($K^+$) cation.

In the cases where $R_6$ and/or $R_7$ denotes an organic or metal cation, the group —$(CH_2)_n$—P(=O)($OR_6$)($OR_7$) may be represented by one of the following three formulae:

the designation "Cation" necessarily implying a positive charge.

The term "aryloxy" denotes an aryl radical bonded to an oxygen atom.

A 5-membered aromatic or nonaromatic heterocycle comprising one or more heteroatoms chosen from N, O or S denotes, for example, pyrrole, imidazole, furan, pyrroline, pyrrolidine, tetrahydrofuran, thiophene, tetrahydrothiophene, pyrazole, oxazole, isoxazole, pyrazoline, imidazoline, pyrazolidine, imidazolidine, dioxolane, thiazole, thiazolidine, isoxazolidine, triazole, oxadiazole, furazane, thiadiazole or tetrazole.

A 6-membered aromatic or nonaromatic heterocycle comprising one or more heteroatoms chosen from N, O or S denotes, for example, pyridine, pyran, dihydropyran, piperidine, pyridazine, pyrimidine, pyrazine, oxazine, dioxine, piperazine, morpholine, dioxane, thiazine, thiomorpholine, oxathiane, dithiane, triazine, trioxane, thiadiazine, dithiazine or trithiane.

According to one embodiment of the invention, for the compounds as defined above, the substituent $R_3$ represents a hydrogen or a 5-membered or 6-membered aromatic or nonaromatic heterocycle comprising one or more heteroatoms chosen from N, O or S, said heterocycle possibly being substituted with a substituent $R_4$ as defined above.

By way of example of a 5-membered heterocycle, mention may be made of a pyrrole or an imidazole, said pyrrole or imidazole possibly being substituted with a substituent $R_4$ chosen from H or —$(CH_2)_n$—P(=O)($OR_6$)($OR_7$) as defined above.

According to a further embodiment of the invention, for the compounds as defined above:

$R_1$ represents hydrogen, (—$NH_2$), (—$NHR_9$), (—$NR_9R'_9$), (—$NHCOR_9$) or (—$N(COR_9)(COR'_9)$), $R_2$ represents hydrogen, benzyl or phenyl, Z represents hydrogen, benzyl, phenyl, —$(CH_2)_n$—$OR_5$, —$(CH_2)_{n1}$—O—$(CH_2)_{n2}R_5$, —$(CH_2)_{n'}$—$COOR_5$ or —$(CH_2)_n$—P(=O)($OR_6$)($OR_7$) with:

n, $n_1$, $n_2$ and n', which may be identical or different, representing, independently of one another, an integer equal to 1 or 2, $R_5$ representing hydrogen, ethyl, acetyl (—$COCH_3$) or phenyl, $R_6$ and $R_7$, which may be identical or different, representing, independently of one another, hydrogen, methyl, ethyl, a sodium cation ($Na^+$) or a lithium cation ($Li^+$), X represents C=O, $SO_2$, Y represents hydrogen.

A subject of the present invention is more particularly a compound as defined above, characterized in that it is chosen from the group comprising:

9H-purin-6-yl-[1,1'-biphenyl]-2-carboxamide,
9H-purin-6-yl-[1,1'-biphenyl]-3-carboxamide,
9H-purin-6-yl-[1,1'-biphenyl]-3'-N-pyrrole-2-carboxamide,
9H-purin-6-yl-[1,1'-biphenyl]-4'-N-pyrrole-2-carboxamide,
9H-purin-6-yl-[1,1'-biphenyl]-3'-N-pyrrole-3-carboxamide,
9H-purin-6-yl-[1,1'-biphenyl]-4'-N-pyrrole-3-carboxamide,
9H-purin-6-yl-[1,1'-biphenyl]-3'-N-pyrrole-4-carboxamide,
9H-purin-6-yl-[1,1'-biphenyl]-4'-N-pyrrole-4-carboxamide,
9H-purin-6-yl-[1,1'-biphenyl]-3'-N-imidazole-2-carboxamide,
9H-purin-6-yl-[1,1'-biphenyl]-4'-N-imidazole-2-carboxamide,
9H-purin-6-yl-[1,1'-biphenyl]-3'-N-imidazole-3-carboxamide,
9H-purin-6-yl-[1,1'-biphenyl]-4'-N-imidazole-3-carboxamide,
9H-purin-6-yl-[1,1'-biphenyl]-3'-$C_4$-imidazole-2-carboxamide,
9H-purin-6-yl-[1,1'-biphenyl]-4'-$C_4$-imidazole-2-carboxamide,
9H-purin-6-yl-[1,1'-biphenyl]-3'-$C_4$-imidazole-3-carboxamide,
9H-purin-6-yl-[1,1'-biphenyl]-4'-$C_4$-imidazole-3-carboxamide,
9H-purin-6-yl-[1,1'-biphenyl]-4'-$C_4$—($N_1$-ethoxyphosphinylmethyl)imidazole-3-carboxamide,
7-(phenylmethyl)-7H-purin-6-yl-[1,1'-biphenyl]-3-carboxamide,
9-(phenylmethyl)-9H-purin-6-yl-[1,1'-biphenyl]-3-carboxamide, 7-[(phenylmethoxy)methyl]-7H-purin-6-yl-[1,1'-biphenyl]-3-carboxamide,
9-[(phenylmethoxy)methyl]-9H-purin-6-yl-[1,1'-biphenyl]-3-carboxamide,
9-[2-(acetyloxy)ethyl]-9H-purin-6-yl-[1,1'-biphenyl]-3-carboxamide,
9-(2-hydroxyethyl)-9H-purin-6-yl-[1,1'-biphenyl]-3-carboxamide,
ethyl 2-[(1,1'-biphenyl)-3-carbonylamino-9H-purin-6-yl]acetate,
2-[(1,1'-biphenyl)-3-carbonylamino-9H-purin-6-yl]acetic acid,
diethyl [(1,1'-biphenyl)-3-carbonylamino-9H-purin-6-yl]methylphosphonate,
[(1,1'-biphenyl)-3-carbonylamino-9H-purin-6-yl]methylphosphonic acid, and mixtures thereof.

The invention also relates to a compound as defined above, for use thereof as a medicament, and preferably for use thereof in the treatment of cancer.

A subject of the present invention is also a compound which has a 6-aminopurine backbone, characterized in that it has formula (I):

wherein
$R_1$, $R_2$, $R_3$, X, Y and Z are as previously defined,
Ar represents a biphenyl or a naphthyl, said biphenyl or naphthyl possibly being substituted with a substituent $R_3$, with $R_3$ being as previously defined,
$R_3$ being bonded to Ar in the ortho, meta or para position,
X being bonded to Ar in the ortho, meta or para position,
said compound of formula (I) being intended for use in the treatment of cancer.

It should be understood that the compound 9H-purin-6-yl-[1,1'-biphenyl]-4-carboxamide clearly falls within general formula (I) as described above and, according to the invention, is intended for use in the treatment of cancer.

By way of examples of compounds (I) which can be advantageously used in the treatment of cancer, mention may be made, in addition to the specifically mentioned 27 compounds above, of:
9H-purin-6-yl-[1,1'-biphenyl]-4-carboxamide,
9H-purin-6-yl-naphthalene-1-carboxamide,
9H-purin-6-yl-naphthalene-2-carboxamide,
(naphthalene-1-carbonylamino-9H-purin-6-yl)methylphosphonic acid,
(naphthalene-2-carbonylamino-9H-purin-6-yl)methylphosphonic acid,
9H-purin-6-yl-[1,1'-biphenyl]-4-sulfonamide,
and mixtures thereof.

By way of cancers which can be treated using the compounds of formula (I), mention may be made of those chosen from:
solid tumors, such as glandular, skin, mesenchymal, genital and neurological cell tumors, or
acute hemopathies (such as acute myeloblastic leukemias and acute lymphoblastic leukemias), chronic myeloproliferative syndromes and chronic lymphoproliferative syndromes (such as Hodgkin's or non-Hodgkin's malignant lymphomas), chronic lymphoid leukemia, hairy cell leukemia and multiple myeloma.

A subject of the invention is also a compound of formula (I) for use as defined above, and more particularly for inhibiting at least one 5'-nucleotidase chosen from cytosolic 5'-nucleotidase II (cN-II), cytosolic 5'-nucleotidase IA (cN-IA), cytosolic 5'-nucleotidase IB (cN-IB), cytosolic 5'-nucleotidase IIIA (cN-IIIA), cytosolic 5'-nucleotidase IIIB (cN-IIIB), ecto-5'-nucleotidase (eN, CD73), cytosolic 5'(3')-deoxynucleotidase (cdN) or mitochondrial 5'(3')-deoxynucleotidase (mdN), and in particular cytosolic 5'-nucleotidase II.

According to one embodiment of the invention, at least one compound of formula (I) may be used in combination with at least one nucleoside analog and/or at least one nucleobase analog for potentiating the anticancer effect of said nucleoside analog and/or of said nucleobase analog. Thus, the invention relates to a compound of formula (I) for use as defined above, characterized in that said compound of formula (I) is combined with at least one nucleoside analog and/or at least one nucleobase analog for potentiating the anticancer effect of said nucleoside analog and/or of said nucleobase analog.

The nucleoside analog used in combination with the compound of formula (I) may for example be chosen from cladribine, fludarabine, clofarabine, cytarabine, gemcitabine, nelarabine, floxuridine or pentostatin.

The nucleobase analog used in combination with a compound of formula (I) may for example be chosen from fluorouracil, 6-mercaptopurine or 6-thioguanosine.

A subject of the invention is also a composition comprising:
at least one compound of formula (I) as previously defined, in combination with:
at least one nucleoside analog chosen from cladribine, fludarabine, clofarabine, cytarabine, gemcitabine, nelarabine, floxuridine or pentostatin, and/or
at least one nucleobase analog chosen from fluorouracil, 6-mercaptopurine or 6-thioguanosine,
and optionally at least one pharmaceutically acceptable excipient.

In the remainder of the text, the expression "composition of the invention" denotes the composition as defined above.

The compounds of formula (I) which can advantageously be used in a composition of the invention are more particularly the compositions specifically mentioned above.

A subject of the invention is also the composition as defined above, for use thereof as a medicament, and preferably in the treatment of cancer.

Typically, the composition of the invention as defined above may be used for simultaneous, separate or sequential administration in the treatment of cancer.

The examples of cancers that may more particularly be treated using a composition of the invention are those described above, namely:
solid tumors, such as glandular, skin, mesenchymal, genital and neurological cell tumors, or
acute hemopathies (such as acute myeloblastic leukemias and acute lymphoblastic leukemias), chronic myeloproliferative syndromes and chronic lymphoproliferative syndromes (such as Hodgkin's or non-Hodgkin's malignant lymphomas), chronic lymphoid leukemia, hairy cell leukemia and multiple myeloma.

The form of the pharmaceutical compositions, their route of administration, their dosage and their dosage regimen naturally depend on the severity of the pathological condition, on its stage of progression, on the age, sex and weight of the subject to be treated, etc.

Those skilled in the art will therefore take care to adapt the dosages according to the patient to be treated.

The pharmaceutical compositions according to the invention can be formulated for topical, oral, systemic, percutaneous, transdermal, parenteral (namely intravenous, intramuscular, subcutaneous, intradermal) administration or the like. Depending on the mode of administration, the composition according to the invention may be in any of the galenical forms.

For oral administration, the composition of the invention may be in the form of tablets, gel capsules, sugar-coated tablets, syrups, suspensions, solutions, powders, granules, emulsions, or lipid or polymeric microspheres or nanospheres or vesicles allowing controlled release.

For parenteral administration, the composition according to the invention may in particular be in the form of an aqueous solution or a dispersion of lotion or serum type, and will be packaged in the form of vials, drip bottles, etc.

These compositions are prepared according to the usual methods known to those skilled in the art.

The invention further relates to a compound of formula (I) as defined above, in combination with at least one compound chosen from the group comprising:
a compound of formula (I),
a nucleoside analog chosen from cladribine, fludarabine, clofarabine, cytarabine, gemcitabine, nelarabine, floxuridine or pentostatin,
a nucleobase analog chosen from fluorouracil, 6-mercaptopurine or 6-thioguanosine,
and mixtures thereof,
for simultaneous, separate or sequential administration in the treatment of cancer.

A subject of the invention is also the use of a compound of formula (I) for producing a medicament, in particular a medicament intended for the treatment of cancer.

Another subject of the invention also relates to methods for treating a subject suffering from a cancer, in particular a cancer as previously defined, comprising the step of administering, to said individual, a therapeutically effective amount of at least one compound of formula (I) or of a composition of the invention.

The term "therapeutically effective amount" is intended to mean an amount sufficient to treat and/or stop the progression of said cancer.

A subject of the invention is also a process for preparing a compound of formula (I), characterized in that:
a 6-aminopurine compound of formula (II):

wherein $R_1$, $R_2$ and Z are as previously defined, is reacted with:
a compound of formula (III):

wherein Ar is a biphenyl or a naphthyl, said biphenyl or naphthyl being substituted on one of its rings with a substituent $R_3$ and on its other ring with a substituent $R_{10}$, namely the compound of formula (III) is represented by one of the formulae below:

with:
$R_3$ as previously defined,
$R_{10}$ represents —COOR$_{11}$, —COR$_{11}$ or —SO$_2$R$_{11}$, with $R_{11}$ representing hydrogen, alkyl, aryl, or halogen.
More particularly, when Ar represents:
a biphenyl, then $R_{10}$ represents —COOR$_{11}$ or —SO$_2$R$_{11}$,
a naphthyl, then $R_{10}$ represents —COR$_{11}$,
with $R_{11}$ as previously defined.

The invention will be understood more clearly in the light of the following nonlimiting and purely illustrative examples.

FIGS. 2 and 3 exemplify the appropriation of a compound of formula (III) wherein Ar represents a biphenyl.

More particularly, FIGS. 2a and 2b exemplify two possible synthesis routes for preparing a compound of formula (III), wherein the biphenyl is substituted on one of its rings with a substituent $R_3$ and on its other ring with a substituent COOR$_{11}$. In FIG. 3, the biphenyl is substituted on one of its rings with a substituent $R_3$ and on its other ring with a substituent COOH.

FIG. 4 illustrates a process for preparing various compounds of formula (I) wherein Y=H, X=(C=O) or SO$_2$, and Ar=biphenyl or naphthyl optionally substituted with a substituent $R_3$, with $R_1$, $R_2$, Z and $R_3$ as previously defined.

More particularly, FIGS. 4a and 4b exemplify the preparation of a compound (I) of the invention wherein Y=H and X=(C=O) and Ar=biphenyl.

Example 1: Illustration of 33 Compounds Corresponding to Formula (I) Defined Above Tables 1 to 4 below exemplify 33 compounds of formula (I) synthesized by the inventors, and denoted respectively (1) to (33) in the subsequent text.

In compounds (1) to (18) of table 1:

$R_1=R_2=Y=Z=H$, X=(C=O) (carbonyl) and Ar=biphenyl, said biphenyl possibly being substituted with a substituent $R_3$, said substituent $R_3$ being chosen from hydrogen, pyrrole or imidazole, said imidazole being optionally substituted with a substituent $R_4$.

The chemical name of compounds (1) to (18) is respectively the following:

9H-purin-6-yl-[1,1'-biphenyl]-2-carboxamide (1),
9H-purin-6-yl-[1,1'-biphenyl]-3-carboxamide (2),
9H-purin-6-yl-[1,1'-biphenyl]-4-carboxamide (3),
9H-purin-6-yl-[1,1'-biphenyl]-3'-N-pyrrole-2-carboxamide (4),
9H-purin-6-yl-[1,1'-biphenyl]-4'-N-pyrrole-2-carboxamide (5),
9H-purin-6-yl-[1,1'-biphenyl]-3'-N-pyrrole-3-carboxamide (6),
9H-purin-6-yl-[1,1'-biphenyl]-4'-N-pyrrole-3-carboxamide (7),
9H-purin-6-yl-[1,1'-biphenyl]-3'-N-pyrrole-4-carboxamide (8),
9H-purin-6-yl-[1,1'-biphenyl]-4'-N-pyrrole-4-carboxamide (9),
9H-purin-6-yl-[1,1'-biphenyl]-3'-N-imidazole-2-carboxamide (10),
9H-purin-6-yl-[1,1'-biphenyl]-4'-N-imidazole-2-carboxamide (11),
9H-purin-6-yl-[1,1'-biphenyl]-3'-N-imidazole-3-carboxamide (12),
9H-purin-6-yl-[1,1'-biphenyl]-4'-N-imidazole-3-carboxamide (13),
9H-purin-6-yl-[1,1'-biphenyl]-3'-$C_4$-imidazole-2-carboxamide (14),
9H-purin-6-yl-[1,1'-biphenyl]-4'-$C_4$-imidazole-2-carboxamide (15),
9H-purin-6-yl-[1,1'-biphenyl]-3'-$C_4$-imidazole-3-carboxamide (16),
9H-purin-6-yl-[1,1'-biphenyl]-4'-$C_4$-imidazole-3-carboxamide (17),
9H-purin-6-yl-[1,1'-biphenyl]-4'-$C_4$—($N_1$-ethoxyphosphinylmethyl)imidazole-3-carboxamide (18).

The orientation indicated in table 1 (ortho, meta or para) respectively for the —NH—(C=O)— group and for the $R_3$ group relates to the position of each of these groups relative to the biphenyl.

TABLE 1

| —NH—(C=O)— orientation | $R_3$/orientation | | $R_4$ | Compounds (I) Numbers |
|---|---|---|---|---|
| ortho | —H | | / | (1) |
| meta | —H | | / | (2) |
| para | —H | | / | (3) |
| ortho |  | meta | / | (4) |
| ortho |  | para | / | (5) |
| meta |  | meta | / | (6) |
| meta |  | para | / | (7) |
| para |  | meta | / | (8) |
| para |  | para | / | (9) |
| ortho |  | meta | / | (10) |
| ortho |  | para | / | (11) |
| meta |  | meta | / | (12) |

TABLE 1-continued

| —NH—(C=O)— orientation | R₃/orientation | | R₄ | Compounds (I) Numbers |
|---|---|---|---|---|
| meta |  | para | / | (13) |
| ortho |  | meta | —H | (14) |
| ortho |  | para | —H | (15) |
| meta |  | meta | —H | (16) |
| meta |  | para | —H | (17) |
| meta |  | meta | —CH₂—P(=O)(ONa)OEt | (18) |

In compounds (19) to (28) of table 2:
$R_1=R_2=Y=H$, X=(C=O) (carbonyl), and Ar=unsubstituted biphenyl.

The chemical name of compounds (19) to (28) is respectively the following:
7-(phenylmethyl)-7H-purin-6-yl-[1,1'-biphenyl]-3-carboxamide (19),
9-(phenylmethyl)-9H-purin-6-yl-[1,1'-biphenyl]-3-carboxamide (20),
7-[(phenylmethoxy)methyl]-7H-purin-6-yl-[1,1'-biphenyl]-3-carboxamide (21),
9-[(phenylmethoxy)methyl]-9H-purin-6-yl-[1,1'-biphenyl]-3-carboxamide (22),
9-[2-(acetyloxy)ethyl]-9H-purin-6-yl-[1,1'-biphenyl]-3-carboxamide (23),
9-(2-hydroxyethyl)-9H-purin-6-yl-[1,1'-biphenyl]-3-carboxamide (24),
ethyl 2-[(1,1'-biphenyl)-3-carbonylamino-9H-purin-6-yl]acetate (25),
2-[(1,1'-biphenyl)-3-carbonylamino-9H-purin-6-yl]acetate (26),
diethyl [(1,1'-biphenyl)-3-carbonylamino-9H-purin-6-yl]methylphosphonate (27),
[(1,1'-biphenyl)-3-carbonylamino-9H-purin-6-yl]methylphosphonic acid (28).

The orientation of the —NH—(C=O)— group indicated (ortho, meta or para) relates to the position of said group relative to the biphenyl.

TABLE 2

| Z | —NH—(C=O)— orientation | Compounds (I) Numbers |
|---|---|---|
| —CH₂Ph (N₇) | meta | (19) |
| —CH₂Ph (N₉) | meta | (20) |
| —CH₂—O—CH₂Ph (N₇) | meta | (21) |
| —CH₂—O—CH₂Ph (N₉) | meta | (22) |

TABLE 2-continued

| Z | —NH—(C=O)— orientation | Compounds (I) Numbers |
|---|---|---|
| —(CH₂)₂—O—Ac (N₉) | meta | (23) |
| —(CH₂)₂—OH (N₉) | meta | (24) |
| —CH₂—COOEt (N₉) | meta | (25) |
| —CH₂—COOH (N₉) | meta | (26) |
| —CH₂—P(=O)(OEt)₂ (N₉) | meta | (27) |
| —CH₂—P(=O)(OH)₂ (N₉) | meta | (28) |

N₇ or N₉ indicate the position of the substituent Z on the nitrogen respectively in position 7 or 9 of the aminopurine compound (I).

In compounds (29) to (32) of table 3:
$R_1=R_2=Y=H$, X=(C=O) (carbonyl), and Ar=unsubstituted naphthyl.

The definition of Z is indicated in table 3 for each of compounds (29) to (32).

The chemical name of compounds (29) to (32) is respectively the following:
9H-purin-6-yl-naphthalene-1-carboxamide (29),
9H-purin-6-yl-naphthalene-2-carboxamide (30),
(naphthalene-1-carbonylamino-9H-purin-6-yl)methylphosphonic acid (31),
(naphthalene-2-carbonylamino-9H-purin-6-yl)methylphosphonic acid (32).

The orientation of the —NH—(C=O)— group indicated (1 or 2) in table 3 relates to the position of said group relative to the naphthyl.

TABLE 3

| Z | —NH—(C=O)— orientation | Compounds (I) Numbers |
|---|---|---|
| H | 1 | (29) |
| H | 2 | (30) |

TABLE 3-continued

| Z | —NH—(C=O)— orientation | Compounds (I) Numbers |
|---|---|---|
| —$CH_2$—P(=O)(OH)$_2$ ($N_9$) | 1 | (31) |
| —$CH_2$—P(=O)(OH)$_2$ ($N_9$) | 2 | (32) |

In compound (33) of table 4:
$R_1$=$R_2$=Y=H, X=(SO$_2$) (sulfonyl), and Ar=unsubstituted biphenyl.

The chemical name of compound (33) is the following: 9H-purin-6-yl-[1,1'-biphenyl]-4-sulfonamide (33).

TABLE 4

| Z | —NH—(SO$_2$)— orientation | Compound (I) Number |
|---|---|---|
| H | para | (33) |

The orientation of the —NH—(SO$_2$)— group indicated (para) in table 4 relates to the position of said group relative to the biphenyl.

Example 2: Synthesis of Compounds of Formula (I)

Figure 1:
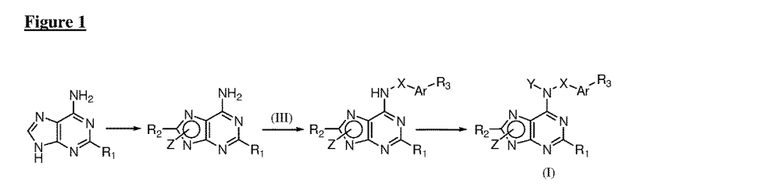
FIG. 1 illustrates the general synthesis scheme for the compounds of formula (I), wherein $R_1$, $R_2$, X, Y, Z, Ar and $R_3$ are as previously defined. The compound of formula (III) is as previously defined.

FIG. 1 is a synthesis scheme which recaps and generalizes all of the steps described below.

Synthesis of the Compounds of Formula (I) Wherein Y=H, X=(C=O) or SO$_2$, and Ar=Biphenyl or Naphthyl Optionally Substituted with a Substituent $R_3$.

Figure 2A:
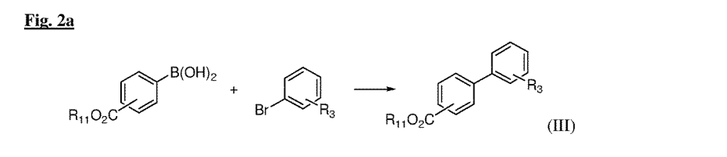
Figure 2B:
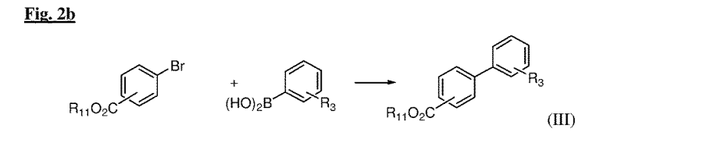

1) Preparation of the biphenyl compound of formula (III) wherein $R_{10}$=COOR$_{11}$ (FIGS. 2a and 2b).

According to the definition of the substituents $R_3$ or $R_{10}$, those skilled in the art will adjust the experimental conditions described below.

Synthesis of the Compound (III) Wherein Ar=Biphenyl (FIG. 2a)

Pd(PPh$_3$)$_4$ (tetrakis (triphenylphosphine)palladium) (0.1 eq.), DMF (dimethylformamide) and phenyl bromide substituted with an $R_3$ (1 eq.) (FIG. 2a) are added, under an argon atmosphere, to a three-necked round-bottomed flask.

Potassium carbonate K$_2$CO$_3$ (3 eq.) and the corresponding ethoxycarbonyl benzeneboronic derivative (1.7 eq.) are then successively added. The mixture is stirred under argon at 100° C., until thin layer chromatography (TLC) reveals that the starting product has been consumed. The mixture is cooled to ambient temperature, and diluted with water and the product is extracted with ethyl acetate (EtOAc). The combined organic phases are washed with brine, dried over sodium sulfate (Na$_2$SO$_4$) and filtered. The solvent is eliminated under vacuum and the residue is purified by silica gel column chromatography, elution being carried out for example with a dichloromethane/methanol mixture (DCM/MeOH: 100/0 to 95/5), to give the expected methyl ester or ethyl ester compound (III) in the form of an oil (FIG. 2a).

Synthesis of the Compound (III) Wherein Ar=Biphenyl (FIG. 2b)

Pd$_2$(dba)$_3$ (tris(dibenzylideneacetone)dipalladium) (0.1 eq.), DMF (dimethylformamide) and methyl or ethyl benzoate bromide (1 eq.) (FIG. 2b) are added, under an argon atmosphere, to a three-necked round-bottomed flask.

Potassium carbonate K$_2$CO$_3$ (3 eq.) and the benzeneboronic derivative substituted with an $R_3$ (1.2 eq.) are then successively added. The mixture is stirred under argon at 100° C., until thin layer chromatography (TLC) reveals that the starting product has been consumed. The mixture is cooled to ambient temperature, diluted with water, and neutralized by adding a hydrochloric acid solution (1M) and the product is extracted with ethyl acetate (EtOAc). The combined organic phases are washed with brine, dried over sodium sulfate (Na$_2$SO$_4$) and filtered. The solvent is eliminated under vacuum and the residue is purified by silica gel column chromatography, elution being carried out for example with a petroleum ether/dichloromethane mixture (PE/DCM: 100/0 to 20/80), to give the expected methyl ester or ethyl ester compound (III) in the form of an oil (FIG. 2b).

Figure 3:
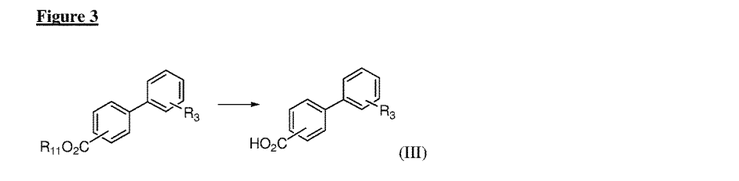

2) Preparation of the Biphenyl Compound (III) Wherein $R_{10}$=COOH (FIG. 3).

A solution of sodium hydroxide (2M NaOH) in water is added dropwise to a solution or suspension of the methyl or ethyl ester compound (III) as obtained in the previous step (point 1) above) in a 1,4-dioxane/ethanol mixture (2/1, v/v). The mixture is stirred at 50° C. until TLC reveals that the reaction is complete. An aqueous hydrochloric acid solution (1M HCl) is then added until the pH is equal to 3, and the mixture is extracted with EtOAc. The combined organic faces are washed with brine, dried over Na$_2$SO$_4$ and filtered. The solvent is eliminated under vacuum and the residue is purified by silica gel column chromatography, elution being carried out for example with DCM/MeOH (100/0 to 90/10) to give the expected carboxylic acid compound (III) in the form of a white powder (FIG. 3).

Figure 4A:
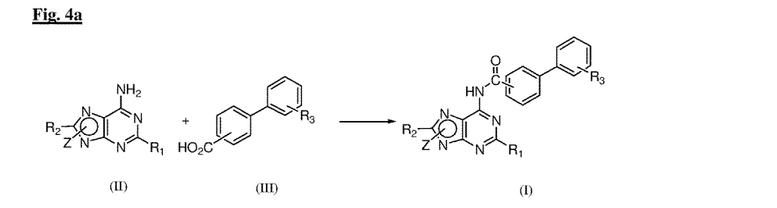
Figure 4B:
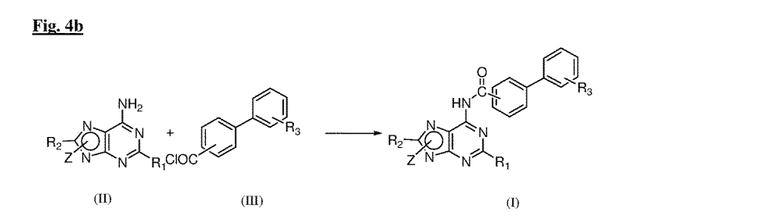

3) Preparation of a Compound of Formula (I) Wherein Y=H, X=CO and Ar=Biphenyl (FIGS. 4a and 4b).

According to the definition of the substituents $R_1$, $R_2$, Z and $R_3$, those skilled in the art will choose the starting products and will if necessary adjust the experimental conditions described below.

Synthesis of the Compound (I) as Exemplified in FIG. 4a

An appropriate coupling reagent, for instance a carbonyl diimidazole/dimethylaminopyridine mixture (CDI (2 eq.)/ DMAP (0.2 eq.)), is added to a solution, with stirring, of the carboxylic acid compound (III) (1 eq.) as obtained in the previous step (point 2) above) in DMF at ambient temperature. After 5 minutes, the 2-aminopurine derivative (2 eq.) of formula (II) is added and the mixture is stirred at 100° C. until the end of the reaction. The solvent is then eliminated under vacuum and the residue is purified by silica gel column chromatography, elution being carried out for example with a DCM/MeOH mixture (100/0 to 90/10) to give the compound of formula (I) of the invention with Y=H and X=CO (FIG. 4a).

Synthesis of the Compound (I) as Exemplified in FIG. 4b

The desired commercial acid chloride compound (III) (1 eq.) is added to a solution, with stirring, of a 2-aminopurine derivative (1.25 eq) of formula (II) in pyridine at ambient temperature. The reaction mixture is stirred at 100° C. until the end of the reaction. The solvent is then eliminated under vacuum and the residue is purified by silica gel column chromatography, elution being carried out for example with DCM/MeOH (100/0 to 90/10) to give the expected compound (I°) (FIG. 4b).

Figure 4C:
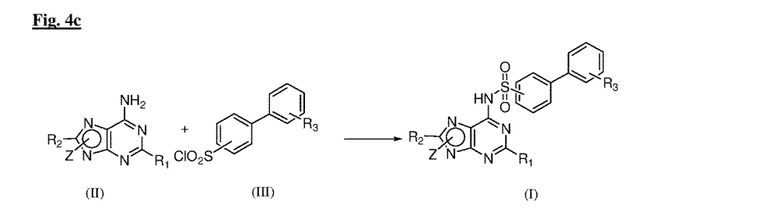
FIG. 4c exemplifies a process for preparing compounds (I) wherein Y=H, X=SO$_2$ and Ar=biphenyl.

4) Preparation of a Compound of Formula (I) Wherein Y=H, X=SO$_2$ and Ar=Biphenyl (FIG. 4c)

The desired commercial sulfuryl chloride compound (III) (1 eq.) is added to a solution, with stirring, of a 2-aminopurine derivative (1.25 eq.) of formula (II) in pyridine at ambient temperature. The reaction mixture is stirred at 100° C. until the end of the reaction. The solvent is then eliminated under vacuum and the residue is purified by silica gel column chromatography, elution being carried out for example with DCM/MeOH (100/0 to 90/10) to give the expected compound (I°) (FIG. 4c).

Figure 4D:
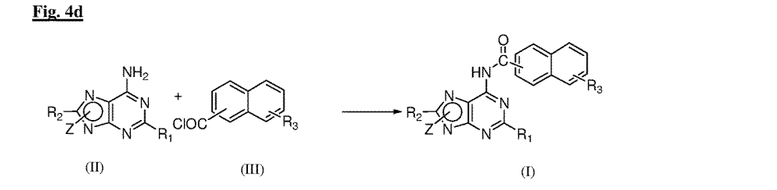
FIG. 4d exemplifies a process for preparing compounds (I) wherein Y=H, X=(C=O) and Ar=naphthyl.

5) Preparation of a Compound of Formula (I) Wherein Y=H, X=CO and Ar=Naphthyl (FIG. 4d)

The desired commercial acid chloride compound (III) (with Ar=naphthyl, see FIG. 4d) (1 eq.) is added to a solution, with stirring, of a 2-aminopurine derivative (1.25 eq.) of formula (II) in pyridine at ambient temperature. The reaction mixture is stirred at 100° C. until the end of the reaction. The solvent is then eliminated under vacuum and the residue is purified by silica gel column chromatography, elution being carried out for example with DCM/MeOH (100/0 to 90/10) to give the expected compound (I°) (FIG. 4d).

Example 3: Determination of the Inhibitory Properties and Cytotoxic Activities of the Compounds (I) of the Invention The inhibitory properties of the compounds (I) of the invention were determined with respect to the purified recombinant target enzyme cN-II (determination of the inhibition of the 5'-nucleotidase activity).

The cytotoxic activities of the compounds of the invention were evaluated in various tumor cell lines (determination of the $IC_{50}$).

A selection of these biological data is presented hereinafter and relates to the compounds (I) of the invention for which an inhibitory activity was measured in vitro but also in cell culture: cytotoxic effect and/or effect of synergy with one of the anticancer molecules chosen from cladribine, fludarabine, clofarabine, cytarabine, gemcitabine, nelarabine, floxuridine or pentostatin (namely nucleoside analogs).

The abbreviations used signify:

cN-II: cytosolic 5'-nucleotidase II,

RL: Human follicular lymphoma cell line used for the cytotoxicity tests (other lines such as CCRF-CEM and MDA-MB-231 were also tested for certain compounds (I) of the invention), Synergy MTT: test for evaluating the cell survival inhibition synergy between the cN-II-inhibiting compounds (I) of the invention and the known anticancer agent (namely a cytotoxic nucleoside analog chosen from cladribine, fludarabine, clofarabine, cytarabine, gemcitabine, nelarabine, floxuridine or pentostatin).

The MTT test described hereinafter makes it possible to evaluate whether the effect is:

1) "additive" in nature: independent effects of the compounds (I) of the invention (cN-II inhibitors) and of the known anticancer agents, 2) "antagonistic" in nature: opposite effects of the compounds (I) of the invention and of the known anticancer agents;

3) "synergistic" in nature: potentiating effect on the known anticancer agent by the cN-II-inhibiting compound (I) of the invention.

It is this third point (synergistic effect) which is investigated in the following text.

Experimental Procedure of the cN-II Inhibition Test:

The activity of cN-II is measured in vitro by following the appearance of the inorganic phosphate produced during the enzymatic reaction. The purified recombinant cN-II enzyme is used in the presence of its preferential substrate, inosine 5'-monophosphate (IMP). During the hydrolysis reaction, inosine and inorganic phosphate are produced from the IMP. This phosphate is then assayed by means of a colorimetric method using Malachite green (kit sold by the company Gentaur): the reading of absorbence at 630 nm makes it possible to quantify the inorganic phosphate.

The same experiment is carried out in the presence of the 5'-nucleotidase-inhibiting compounds (I) of the invention (concentration range from 0 to 2 mM). This "broad" screening test makes it possible to determine the percentage inhibition of cN-II by the compounds (I) in the range of concentrations studied.

Experimental Conditions:

The reagents used are: 50 mM imidazole buffer, pH=6.5, 500 mM NaCl and 10 mM $MgCl_2$. The enzyme (cN-II) concentration is 0.1 μM and the IMP concentration is 100 μM.

An incubation at 37° C. is carried out for 2 to 5 minutes and then stopped by adding the Malachite green reagent which contains a strong acid. A phosphate concentration range is performed in parallel in order to quantify the phosphate produced during the reaction.

For the compounds of the invention which demonstrated a strong inhibition with this first test, a second inhibition test is carried out by measuring the enzymatic kinetics. This longer test makes it possible to characterize the mode of inhibition and to determine the inhibition constant (Ki).

Experimental Procedure of the "Synergy MTT" Test:

For the tests of synergy between the cN-II-inhibiting compounds (I) and the cytotoxic nucleoside analogs, the cells are seeded into 96-well plates containing varied concentrations of the inhibitor (I) alone, of the nucleoside analog alone or of a mixture of the two compounds at a constant ratio (close to the ratio of the $IC_{50}$ values for each compound alone). After 72 h of incubation, the living cells are quantified using the MTT reagent.

The inhibitory concentration 50 ($IC_{50}$) and the combination index ($CI_{95}$) are calculated with the CompuSyn software 1.0 (ComboSyn, Inc., USA).

The $IC_{50}$ corresponds to the concentration of a compound which allows 50% survival of the cells.

The $CI_{95}$ is calculated according to the method of Chou and Talalay[3] with a formula which takes into account the concentrations of the two compounds and the fraction affected at these concentrations (i.e. the dead cells). $CI_{95}$ values below 0.9 indicate synergy between the two compounds, values between 0.9 and 1.1 indicate additivity, and values above 1.1 indicate antagonism according to the customs in the literature[4] and the software manual (Compusyn user's guide). This method is the reference method in the evaluation of interactions between molecules[3, 5, 6, 7].

Table 5 below groups together all of the experimental data obtained regarding the inhibitory activity of about twenty compounds of formula (I) of the invention.

TABLE 5

| Comp.(I) tested (N°) | Inhibition cN-II in vitro (200 μM) | $K_i$ (mM) | Inhibition strength (Strong/Medium/Weak) | RL cancer line $IC_{50}$ (μM) | Synergy MTT |
|---|---|---|---|---|---|
| (1) | 17 | n.d.* | W/70% inh. at 1 mM | 165 | Additive with cladribine |
| (5) | 87 +/− 3% | n.d. | S | 51 | Additive with cladribine |
| (4) | 69 +/− 9 | n.a. | S | 25 | Additive with cladribine |
| (11) | 0% | n.d. | W/42% inh. at 0.8 mM | 51 | Antagonistic with cladribine & clofarabine Additive with fludarabine |
| (15) | 0% | n.d. | W/58% inh. at 0.8 mM | 107 | n.d. |
| (10) | 13% | n.d. | W/25% inh. at 0.8 mM | 168 +/− 56 | n.d. |
| (14) | 7-40% | n.d. | W/not reproducible | 215 +/− 13 | n.d. |
| (6) | 56 +/− 13% | 1.53 | S | 11 +/−4 | Antagonistic with cladribine, clofarabine, fludarabine |
| (7) | 28% | n.d. | M | n.d | n.d. |
| (2) | 60 +/− 5% | 0.8 | S/competitive | 25 | Synergy with cladribine & clofarabine |
| (13) | 10% | n.d. | W | 203 | n.d. |
| (12) | 39 +/− 11% | n.d. | W | 34 | Synergy with cladribine & clofarabine Antagonistic with fludarabine |
| (16) | 47 +/− 12% | n.d. | W | 53 | Synergy with clofarabine Antagonistic with fludarabine |
| (17) | 21 +/− 10% | n.d. | W | 5 | Synergy with clofarabine Antagonistic with fludarabine |
| (19) | 68 +/− 15% | n.d. | S | 60 | Synergy with cladribine & fludarabine |
| (20) | 58 +/−19% | n.d. | S | 51 | Antagonistic with cladribine & clofarabine Synergy with fludarabine |
| (22) | 43 +/− 7% | n.d. | M | 188 +/− 33 | n.d. |
| (21) | 50 +/− 2% | n.d. | M | 36 +/− 5 | Synergy with cladribine & clofarabine Additive with fludarabine |
| (3) | 60 +/− 5% | 0.8 | S/competitive | 128 | n.d. |
| (9) | 0% | n.d. | No effect/Insoluble | 98 | Synergy with cladribine Antagonistic with fludarabine |
| (29) | 40 +/− 10% | n.d. | M | 130 | n.d. |
| (30) | 35 +/− 10% | n.d. | M | 58 | n.d. |
| (31) | 10% | n.d. | W | 250 | n.d. |
| (32) | 10% | n.d. | W | 145 | n.d. |
| (33) | 70 +/− 5% | n.d. | S | 195 | n.d. |

*n.d.: not determined; n.a.: not applicable since compound insoluble in the reaction buffer.

Conclusion

Compounds (2), (9), (12), (16), (17), (19), (20) and (21) show a synergistic effect with at least one of the three anticancer agents of the prior art.

Compounds (2), (4), (6), (12), (17) and (21) also show intrinsic cytotoxic activity on the cell model used, with $IC_{50}$ values of about a few micromolar to a few tens of micromolar.

Example 4: Evaluation of the In Vivo Antitumor Activity and Ex Vivo Cytotoxic Activity of a Compound of the Invention The antitumor properties of compound (2) of the invention, namely 9H-purin-6-yl-[1,1'-biphenyl]-3-carboxamide, were determined in a syngeneic model of an intraperitoneal tumor in mice.

Figure 5:
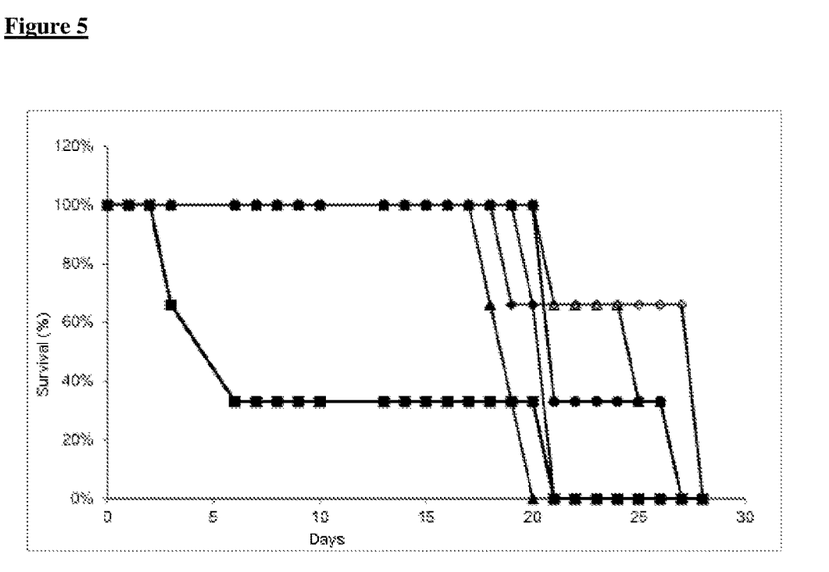
FIG. 5 illustrates the survival of B6D2F1 mice having received L1210 cells and treated with:
cyclodextrins alone (■),
fludarabine (100 mg/kg) (●),
compound (2) of the invention alone (3.94 mg/kg) (▲) or in combination with fludarabine (100 mg/kg) (Δ),
compound (2) of the invention alone (7.89 mg/kg) (♦) or in combination with fludarabine 100 mg/kg (◊).

Experimental Procedure of the In Vivo Evaluation:

In order to obtain solutions of compound (2) at concentrations compatible with the in vivo evaluations, compound (2) is solubilized at 10 mM using 2,6-diO-methyl-beta-cyclodextrins. L1210 murine leukemia cells (1 million) are injected into the intraperitoneal cavity of four-week-old B6D2F1 mice (three mice per group) on day 1, and the mice are treated on days 2, 4, 7, 9 and 11 with fludarabine (100 mg/kg), compound (2) (7.89 mg/kg or 3.94 mg/kg), a combination of fludarabine and compound (2) or a solution of cyclodextrins alone. The survival of the mice is used as final point of the experiment (see FIG. 5).

Conclusion:

An increase in the dose of compound (2) from 3.94 to 7.89 mg/kg makes it possible to prolong the survival of the mice, indicating a dose-effect in this range.

The combination between compound (2), in particular at 7.89 mg/kg, and fludarabine at 100 mg/kg makes it possible to prolong the survival of the mice compared with fludarabine alone, indicating a potentiating effect of this combination.

Figure 6:
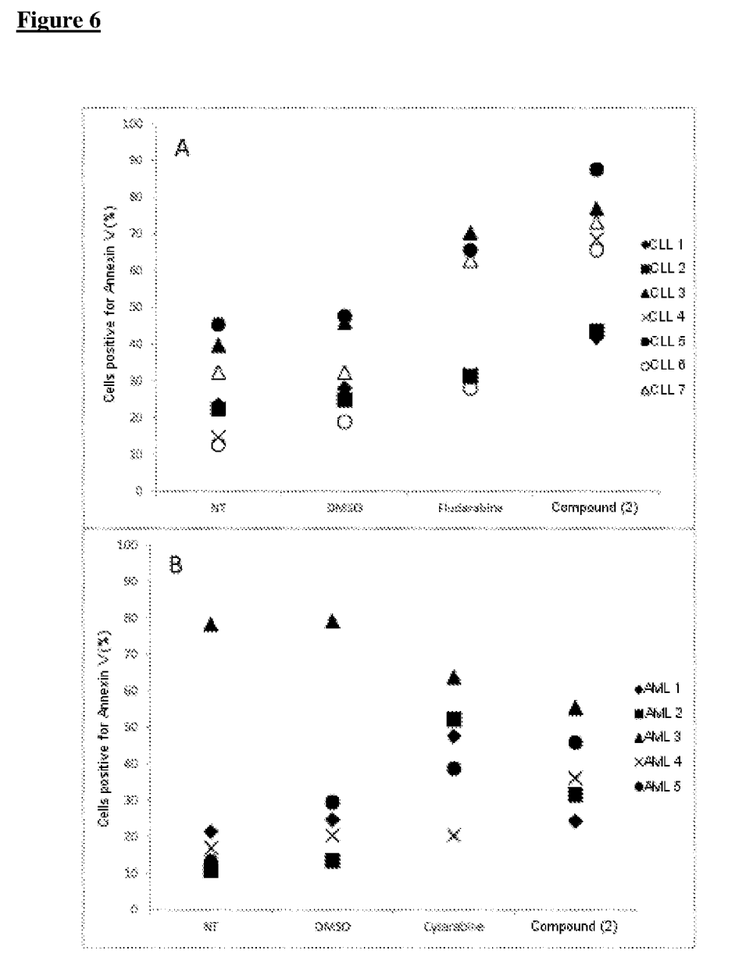
FIG. 6 illustrates the percentage of Annexin V labeling for cells of CLL (FIG. 6A) and AML (FIG. 6B) patients, incubated with the presence of DMSO, of fludarabine (10 μM), of cytarabine (100 μM) or of compound (2) of the invention (100 μM).

Experimental Procedure of the Ex Vivo Evaluation:

Peripheral blood was recovered from patients suffering from chronic lymphoblastic leukemia (LLC) or from acute myeloid leukemia (AML) in heparinized tubes. After lysis of the red blood cells, the blood is incubated for 24 hours in the presence of DMSO, of 10 µM fludarabine, of 100 µM cytarabine or of 100 µM compound (2) of the invention, before determination of the induction of apoptosis and of cell death with the Annexin V and propidium iodide labels by flow cytometry. The cells having experienced an effect of the incubations are labeled with Annexin V alone or with propidium iodide (see FIG. 6).

Conclusion:

All the CLL examples are more sensitive to incubation with 100 µM of compound (2) of the invention than to incubation with 10 µM of fludarabine (65.3% compared with 45.8%), thereby indicating good cytotoxicity of compound (2) for these cells.

For the AML samples, two out of five are more sensitive to 100 µM of compound (2) than to 100 µM of cytarabine, with a mean over the five samples in favor of cytarabine (44.5% compared with 38.6%).

General Conclusion

The originality of the invention is based on the nature of the pharmacological target (cytosolic and non-membrane). No intracellular (cytosolic) 5'-nucleotidase inhibitor is to date described in the treatment of human pathological conditions.

The hitherto unpublished combination of the compounds of the invention, which are 5'-nucleotidase inhibitors, and in particular cN-II inhibitors, with cytotoxic nucleoside analogs which are known at the current time, makes it possible to increase the efficacy of this drug class via several mechanisms: (1) via intrinsic inhibition of cN-II inducing a mechanism of apoptosis; (2) by increasing the intracellular concentration of the phosphorylated (nucleotide) forms of the nucleoside analog, which forms are responsible for its antiproliferative activity; (3) by making it possible to respond to certain mechanisms of cell resistance associated with the overexpression of cN-II.

LITERATURE REFERENCES

1. Fakhoury M., De Beaumais T., Médard Y. & Jacqz-Aigrain E. (2010). Suivi thérapeutique pharmacologique des 6-thioguanine nucléotides dans les leucémies aigues lymphoblastiques de l'enfant: intérêt and limites [Pharmacological therapeutic monitoring of 6-thioguanine nucleotides in acute lymphoblastic leukemias in children: advantage and limits]. *Thérapie [Therapy]*, 65 (3): 187-193.
2. a) Tzoneva, G.; Perez-Garcia, A.; Carpenter, Z.; Khiabanian, H.; Tosello, V.; Allegretta, M.; Paietta, E.; Racevskis, J.; Rowe, J. M.; Tallman, M. S.; Paganin, M.; Basso, G.; Hof, J.; Kirschner-Schwabe, R.; Palomero, T.; Rabadan, R. & Ferrando, A. (2013). Activating mutations in the NT5C2 nucleotidase gene drive chemotherapy resistance in relapsed ALL. *Nat Med*, 19 (3), 368-71.
  b) Meyer, J. A.; Wang, J.; Hogan, L. E.; Yang, J. J.; Dandekar, S.; Patel, J. P.; Tang, Z.; Zumbo, P.; Li, S.; Zavadil, J.; Levine, R. L.; Cardozo, T.; Hunger, S. P.; Raetz, E. A.; Evans, W. E.; Morrison, D. J.; Mason, C. E. & Carroll, W. L. (2013). Relapse-specific mutations in NT5C2 in childhood acute lymphoblastic leukemia. *Nat Genet*, 45 (3), 290-4.
3. Chou, T. C. & Talalay, P. (1984). Quantitative analysis of dose-effect relationships: the combined effects of multiple drugs or enzyme inhibitors. *Adv Enzyme Regul* 22, 27-55.
4. Bijnsdorp, I. V., Giovannetti, E. & Peters, G. J. Analysis of drug interactions. *Methods Mol Biol* 731, 421-34.
5. Chou, T. C. (2006). Theoretical basis, experimental design, and computerized simulation of synergism and antagonism in drug combination studies. *Pharmacol Rev* 58, 621-81.
6. Chou, T. C. (2010). Drug combination studies and their synergy quantification using the Chou-Talalay method. *Cancer Res* 70, 440-6.
7. Tallarida, R. J. (2006). An overview of drug combination analysis with isobolograms. *J Pharmacol Exp Ther* 319, 1-7.

The invention claimed is:

1. A compound which has a 6-aminopurine backbone, characterized in that it has the formula:

wherein $R_1$ and $R_2$, which may be identical or different, are, independently of one another, hydrogen, alkyl, alkenyl, alkynyl, aryl, —$COR_9$, —$NH_2$, —$NHR_9$, —$NR_9R'_9$, —$NHCOR_9$, —$N(COR_9)(COR'_9)$, —$CF_3$, halogen, —OH, —$OR_9$, —SH or —$SR_9$, with $R_9$ and $R'_9$, which may be identical or different, are, independently of one another, alkyl, alkenyl, alkynyl or aryl, Z is on either of the positions $N_7$ and $N_9$ of the purine, and is hydrogen, alkyl, alkenyl, alkynyl, aryl, —$COR_9$, halogen, —$(CH_2)_n$—$OR_5$, —$(CH_2)_{n1}$—O—$(CH_2)_{n2}$ $R_5$, —$(CH_2)_{n'}$—$COOR_5$ or —$(CH_2)n$-$P(=O)(OR_6)$ $(OR_7)$, where:

n, $n_1$ and $n_2$, which may be identical or different, are, independently of one another, an integer ranging from 1 to 10 and n' an integer ranging from 0 to 10, $R_5$ is hydrogen, alkyl, alkenyl, alkynyl, aryl or —$COR_9$, $R_6$ and $R_7$, which may be identical or different, are, independently of one another, hydrogen, alkyl, alkenyl, alkynyl, aryl, —$COR_9$, an organic cation or a metal cation, X is a divalent radical chosen from C=O, C=S, C=$NR_8$ and $SO_2$, where:

$R_8$ is hydrogen, alkyl, alkenyl, alkynyl, —OH or —$OR_9$,

Y has the same meaning as $R_5$,

Ar is a biphenyl, $R_3$ is hydrogen, alkyl, alkenyl, alkynyl, aryl, —$NH_2$, —$NHR_9$, —$NR_9R'_9$, —OH, —$OR_9$, aryloxy, —$OCH_2C_6H_5$; a 5-membered or 6-membered aromatic or nonaromatic heterocycle comprising one or more heteroatoms chosen from N, O and S, said 5-membered or 6-membered heterocycle also possibly being substituted with a substituent $R_4$, where:

$R_4$ is hydrogen, alkyl, alkenyl, alkynyl, aryl, —$COR_9$, —$(CH_2)_n$—$OR_5$, —$(CH_2)_{n1}$—O—$(CH_2)_{n2}R_5$, —$(CH_2)_n$—$COOR_5$ or —$(CH_2)_n$—P(=O)($OR_6R_7$), $R_3$ being bonded to Ar in the ortho, meta or para position, X being bonded to Ar in the ortho, meta or para position, with the exception of the compound 9H-purin-6-yl-[1,1'-biphenyl]-4-carboxamide.

2. The compound as claimed in claim 1, wherein the substituent $R_3$ is a hydrogen or a 5-membered or 6-membered aromatic or nonaromatic heterocycle comprising one or more heteroatoms chosen from N, O and S, said heterocycle possibly being substituted with a substituent $R_4$ as defined in claim 1.

3. The compound as claimed in claim 1 wherein the 5-membered heterocycle is a pyrrole or an imidazole, said pyrrole or imidazole possibly being substituted with a substituent $R_4$ chosen from hydrogen and —$(CH_2)_n$—P(=O)($OR_6$)($OR_7$) as defined in claim 1.

4. The compound as claimed in claim 1 wherein:

$R_1$ is hydrogen, (—$NH_2$), (—$NHR_9$), (—$NR_9R'_9$), (—$NHCOR_9$), or (—N($COR_9$)($COR'_9$)), $R_2$ is hydrogen, benzyl or phenyl, Z is hydrogen, benzyl, phenyl, —$(CH_2)_n$—$OR_5$, —$(CH_2)_{n1}$—O—$(CH_2)_{n2}R_5$, —$(CH_2)_{n'}$—$COOR_5$ or —$(CH_2)_n$—P(=O)($OR_6$)($OR_7$) where:

n, $n_1$, $n_2$ and n', which may be identical or different, are, independently of one another, an integer equal to 1 or 2, $R_5$ is hydrogen, ethyl, acetyl (—$COCH_3$) or phenyl, $R_6$ and $R_7$, which may be identical or different, are, independently of one another, hydrogen, methyl, ethyl, a sodium cation ($Na^+$) or a lithium cation (Li+),

X is C=O or $SO_2$,

Y is hydrogen.

5. The compound as claimed in claim 1 selected from the group consisting of:

9H-purin-6-yl-[1,1'-biphenyl]-2-carboxamide,
9H-purin-6-yl-[1,1'-biphenyl]-3-carboxamide,
9H-purin-6-yl-[1,1'-biphenyl]-3'-N-pyrrole-2-carboxamide,
9H-purin-6-yl-[1,1'-biphenyl]-4'-N-pyrrole-2-carboxamide,
9H-purin-6-yl-[1,1'-biphenyl]-3'-N-pyrrole-3-carboxamide,
9H-purin-6-yl-[1,1'-biphenyl]-4'-N-pyrrole-3-carboxamide,
9H-purin-6-yl-[1,1'-biphenyl]-3'-N-pyrrole-4-carboxamide,
9H-purin-6-yl-[1,1'-biphenyl]-4'-N-pyrrole-4-carboxamide,
9H-purin-6-yl-[1,1'-biphenyl]-3'-N-imidazole-2-carboxamide,
9H-purin-6-yl-[1,1'-biphenyl]-4'-N-imidazole-2-carboxamide,
9H-purin-6-yl-[1,1'-biphenyl]-3'-N-imidazole-3-carboxamide,
9H-purin-6-yl-[1,1'-biphenyl]-4'-N-imidazole-3-carboxamide,
9H-purin-6-yl-[1,1'-biphenyl]-3'-C4-imidazole-2-carboxamide,
9H-purin-6-yl-[1,1'-biphenyl]-4'-C4-imidazole-2-carboxamide,
9H-purin-6-yl-[1,1'-biphenyl]-3'-C4-imidazole-3-carboxamide,
9H-purin-6-yl-[1,1'-biphenyl]-4'-C4-imidazole-3-carboxamide,
9H-purin-6-yl-[1,1'-biphenyl]-4'-$C_4$—($N_1$-ethoxyphosphinylmethyl)imidazole-3-carboxamide,
7-(phenylmethyl)-7H-purin-6-yl-[1,1'-biphenyl]-3-carboxamide,
9-(phenylmethyl)-9H-purin-6-yl-[1,1'-biphenyl]-3-carboxamide,
7-[(phenylmethoxy)methyl]-7H-purin-6-yl-[1,1'-biphenyl]-3-carboxamide,
9-[(phenylmethoxy)methyl]-9H-purin-6-yl-[1,1'-biphenyl]-3-carboxamide,
9-[2-(acetyloxy)ethyl]-9H-purin-6-yl-[1,1'-biphenyl]-3-carboxamide,
9-(2-hydroxyethyl)-9H-purin-6-yl-[1,1'-biphenyl]-3-carboxamide,
ethyl 2-[(1,1'-biphenyl)-3-carbonylamino-9H-purin-6-yl] acetate,
2-[(1,1'-biphenyl)-3-carbonylamino-9H-purin-6-yl]acetic acid,
diethyl [(1,1'-biphenyl)-3-carbonylamino-9H-purin-6-yl] methylphosphonate,
[(1,1'-biphenyl)-3-carbonylamino-9H-purin-6-yl]methylphosphonic acid,
and mixtures thereof.

6. A method for the treatment of cancer comprising administering to a subject that has cancer a compound which has a 6-aminopurine backbone, wherein said compound has formula (I):

wherein $R_1$ and $R_2$, which may be identical or different, are, independently of one another, hydrogen, alkyl, alkenyl, alkynyl, aryl, —$COR_9$, —$NH_2$, —$NHR_9$, —$NR_9R'_9$, —$NHCOR_9$, —N($COR_9$)($COR'_9$), —$CF_3$, halogen, —OH, —$OR_9$, —SH or —$SR_9$, with $R_9$ and $R'_9$, which may be identical or different, are, independently of one another, alkyl, alkenyl, alkynyl or aryl, Z is on either of the positions $N_7$ and $N_9$ of the purine, and is hydrogen, alkyl, alkenyl, alkynyl, aryl, —$COR_9$, halogen, —(CH$_2$)$_n$—OR$_5$, —(CH$_2$)$_{n1}$—O—(CH$_2$)$_{n2}$R$_5$, —(CH$_2$)$_n$'—COOR$_5$ or —(CH$_2$)n-P(=O)(OR$_6$)(OR$_7$), where:

n, n$_1$ and n$_2$, which may be identical or different, are, independently of one another, an integer ranging from 1 to 10 and n' an integer ranging from 0 to 10, R$_5$ is hydrogen, alkyl, alkenyl, alkynyl, aryl or —COR$_9$, R$_6$ and R$_7$, which may be identical or different, are, independently of one another, hydrogen, alkyl, alkenyl, alkynyl, aryl, —COR$_9$, an organic cation or a metal cation, X is a divalent radical chosen from C=O, C=S, C=NR$_8$ and SO$_2$, where:

R$_8$ is hydrogen, alkyl, alkenyl, alkynyl —OH or —OR$_9$,

Y has the same R$_5$,

Ar is a biphenyl or a naphthyl,

R$_3$ is hydrogen, alkyl, alkenyl, alkynyl, aryl, —NH$_2$, —NHR$_9$, —NR$_9$R'$_9$, —OH, —OR$_9$, aryloxy, —OCH$_2$C$_6$H$_5$; a 5-membered or 6-membered aromatic or nonaromatic heterocycle comprising one or more heteroatoms chosen from N, O and S, said 5-membered or 6-membered heterocycle also possibly being substituted with a substituent R$_4$, where:

R$_4$ is hydrogen, alkyl, alkenyl, alkynyl, aryl, —COR$_9$, —(CH$_2$)$_n$—OR$_5$, —(CH$_2$)$_{n1}$—O—O—CH$_2$)$_{n2}$R$_5$, —(CH$_2$)$_n$—COOR$_5$ or —CH$_2$)$_n$—P(=O)(OR$_6$R$_7$), R$_3$ being bonded to Ar in the ortho, meta or para position, X being bonded to Ar in the ortho, meta or para position.

7. The method as claimed in claim 6, wherein said compound is chosen from the group:

9H-purin-6-yl-[1,1'-biphenyl]-2-carboxamide,
9H-purin-6-yl-[1,1'-biphenyl]-3-carboxamide,
9H-purin-6-yl-[1,1'-biphenyl]-3'-N-pyrrole-2-carboxamide,
9H-purin-6-yl-[1,1'-biphenyl]-4'-N-pyrrole-2-carboxamide,
9H-purin-6-yl-[1,1'-biphenyl]-3'-N-pyrrole-3-carboxamide,
9H-purin-6-yl-[1,1'-biphenyl]-4'-N-pyrrole-3-carboxamide,
9H-purin-6-yl-[1,1'-biphenyl]-3'-N-pyrrole-4-carboxamide,
9H-purin-6-yl-[1,1'-biphenyl]-4'-N-pyrrole-4-carboxamide,
9H-purin-6-yl-[1,1'-biphenyl]-3'-N-imidazole-2-carboxamide,
9H-purin-6-yl-[1,1'-biphenyl]-4'-N-imidazole-2-carboxamide,
9H-purin-6-yl-[1,1'-biphenyl]-3'-N-imidazole-3-carboxamide,
9H-purin-6-yl-[1,1'-biphenyl]-4'-N-imidazole-3-carboxamide,
9H-purin-6-yl-[1,1'-biphenyl]-3'-C4-imidazole-2-carboxamide,
9H-purin-6-yl-[1,1'-biphenyl]-4'-C4-imidazole-2-carboxamide,
9H-purin-6-yl-[1,1'-biphenyl]-3'-C4-imidazole-3-carboxamide,
9H-purin-6-yl-[1,1'-biphenyl]-4'-C4-imidazole-3-carboxamide,
9H-purin-6-yl-[1,1'-biphenyl]-4'-C$_4$—(N$_1$-ethoxyphosphinylmethyl)imidazole-3-carboxamide,
7-(phenylmethyl)-7H-purin-6-yl-[1,1'-biphenyl]-3-carboxamide,
9-(phenylmethyl)-9H-purin-6-yl-[1,1'-biphenyl]-3-carboxamide,
7-[(phenylmethoxy)methyl]-7H-purin-6-yl-[1,1'-biphenyl]-3-carboxamide,
9-[(phenylmethoxy)methyl]-9H-purin-6-yl-[1,1'-biphenyl]-3-carboxamide,
9-[2-(acetyloxy)ethyl]-9H-purin-6-yl-[1,1'-biphenyl]-3-carboxamide,
9-(2-hydroxyethyl)-9H-purin-6-yl-[1,1'-biphenyl]-3-carboxamide,
ethyl 2-[(1,1'-biphenyl)-3-carbonylamino-9H-purin-6-yl]acetate,
2-[(1,1'-biphenyl)-3-carbonylamino-9H-purin-6-yl]acetic acid,
diethyl [(1,1'-biphenyl)-3-carbonylamino-9H-purin-6-yl]methylphosphonate,
[(1,1'-biphenyl)-3-carbonylamino-9H-purin-6-yl]methylphosphonic acid,
9H-purin-6-ylnaphthalene-1-carboxamide,
9H-purin-6-ylnaphthalene-2-carboxamide,
(naphthalene-1-carbonylamino-9H-purin-6-yl)methylphosphonic acid,
(naphthalene-2-carbonylamino-9H-purin-6-yl)methylphosphonic acid,
9H-purin-6-yl-[1,1'-biphenyl]-4-sulfonamide, and mixtures thereof.

8. The method of claim 6 wherein said method inhibits at least one 5'-nucleotidase chosen from cytosolic 5'-nucleotidase II (cN-II), cytosolic 5'-nucleotidase IA (cN-IA), cytosolic 5'-nucleotidase IB (cN-IB), cytosolic 5'-nucleotidase IMA (cN-IIIA), cytosolic 5'-nucleotidase NIB (cN-IIIB), ecto-5'-nucleotidase (eN, CD73), cytosolic 5'(3')-deoxynucleotidase (cdN) and mitochondrial 5'(3')-deoxynucleotidase (mdN).

9. The method of claim 6, wherein administration of said compound is combined with at least one nucleoside analog and/or at least one nucleobase analog.

10. The method of claim 9, wherein:
the nucleoside analog is chosen from cladribine, fludarabine, clofarabine, cytarabine, gemcitabine, nelarabine, floxuridine and pentostatin,
the nucleobase analog is chosen from fluorouracil, 6-mercaptopurine and 6-thioguanosine.

11. A composition comprising:
at least one compound of formula (I):

wherein
R$_1$ and R$_2$, which may be identical or different, are, independently of one another, hydrogen, alkyl, alkenyl, alkynyl, aryl, —COR$_9$, —NH$_2$, —NHR$_9$, —NR$_9$R'$_9$, —NHCOR$_9$, —N(COR$_9$)(COR'$_9$), —CF$_3$, halogen, —OH, —OR$_9$, —SH or —SR$_9$, with R$_9$ and R'$_9$, which may be identical or different, are, independently of one another, alkyl, alkenyl, alkynyl or aryl, Z is on either of the positions N$_7$ and N$_9$ of the purine, and is hydrogen, alkyl, alkenyl, alkynyl, aryl, —COR$_9$, halogen, —(CH$_2$)$_2$—OR$_5$, —(CH$_2$)$_{n1}$—O—(CH$_2$)$_{n2}$R$_5$—(CH$_2$)$_n$'—COOR$_5$ or –(CH$_2$)n-P(=O)(OR$_6$)(OR$_7$), where:

n, n$_1$ and n$_2$, which may be identical or different, are, independently of one another, an integer ranging from 1 to 10 and n' an integer ranging from 0 to 10, R$_5$ is hydrogen, alkyl, alkenyl, alkynyl, aryl or —COR$_9$, R$_6$ and R$_7$, which may be identical or different, are, independently of one another, hydrogen, alkyl, alkenyl, alkynyl, aryl, —COR$_9$, an organic cation or a metal cation, X is a divalent radical chosen from C=O, C=S, C=NR$_8$ and SO$_2$, where:

R$_8$ is hydrogen, alkyl, alkenyl, alkynyl, —OH or —OR$_9$,

Y has the same R$_5$,

Ar is a biphenyl or a naphthyl,

R$_3$ is hydrogen, alkyl, alkenyl, alkynyl, aryl, —NH$_2$, —NHR$_9$, —NR$_9$R'$_9$, —OH, —OR$_9$, aryloxy, —OCH$_2$C$_6$H$_5$; a 5-membered or 6-membered aromatic or nonaromatic heterocycle comprising one or more heteroatoms chosen from N, O and S, said 5-membered or 6-membered heterocycle also possibly being substituted with a substituent R$_4$, where:

R$_4$ is hydrogen, alkyl, alkenyl, alkynyl, aryl, —COR$_9$, —(CH$_2$)$_n$—OR$_5$, —(CH$_2$)$_{n1}$—O—CH$_2$)$_{n2}$R$_5$, —(CH$_2$)$_n$—COOR$_5$ or —(CH$_2$)$_n$—P(=O)(OR$_6$R$_7$), R$_3$ being bonded to Ar in the ortho, meta or para position, X being bonded to Ar in the ortho, meta or para position, in combination with:
   at least one nucleoside analog chosen from cladribine, fludarabine, clofarabine cytarabine, gemcitabine, nelarabine, floxuridine and pentostatin, and/or
   at least one nucleobase analog chosen from fluorouracil, 6-mercaptopurine and 6-thioguanosine,
   and optionally at least one pharmaceutically acceptable excipient.

12. The composition as claimed in claim 11, wherein the compound of formula (I) is chosen from the group:
9H-purin-6-yl-[1,1'-biphenyl]-2-carboxamide,
9H-purin-6-yl-[1,1'-biphenyl]-3-carboxamide,
9H-purin-6-yl-[1,1'-biphenyl]-3'-N-pyrrole-2-carboxamide,
9H-purin-6-yl-[1,1'-biphenyl]-4'-N-pyrrole-2-carboxamide,
9H-purin-6-yl-[1,1'-biphenyl]-3'-N-pyrrole-3-carboxamide,
9H-purin-6-yl-[1,1'-biphenyl]-4'-N-pyrrole-3-carboxamide,
9H-purin-6-yl-[1,1'-biphenyl]-3'-N-pyrrole-4-carboxamide,
9H-purin-6-yl-[1,1'-biphenyl]-4'-N-pyrrole-4-carboxamide,
9H-purin-6-yl-[1,1'-biphenyl]-3'-N-imidazole-2-carboxamide,
9H-purin-6-yl-[1,1'-biphenyl]-4'-N-imidazole-2-carboxamide,
9H-purin-6-yl-[1,1'-biphenyl]-3'-N-imidazole-3-carboxamide,
9H-purin-6-yl-[1,1'-biphenyl]-4'-N-imidazole-3-carboxamide,
9H-purin-6-yl-[1,1'-biphenyl]-3'-C4-imidazole-2-carboxamide,
9H-purin-6-yl-[1,1'-biphenyl]-4'-C4-imidazole-2-carboxamide,
9H-purin-6-yl-[1,1'-biphenyl]-3'-C-4-imidazole-3-carboxamide,
9H-purin-6-yl-[1,1'-biphenyl]-4'-C4-imidazole-3-carboxamide,
9H-purin-6-yl-[1,1'-biphenyl]-4'-C$_4$—(N$_1$-ethoxyphosphinylmethyl)imidazole-3-carboxamide,
7-(phenylmethyl)-7H-purin-6-yl-[1,1'-biphenyl]-3-carboxamide,
9-(phenylmethyl)-9H-purin-6-yl-[1,1'-biphenyl]-3-carboxamide,
7-[(phenylmethoxy)methyl]-7H-purin-6-yl-[1,1'-biphenyl]-3-carboxamide,
9-[(phenylmethoxy)methyl]-9H-purin-6-yl-[1,1'-biphenyl]-3-carboxamide,
9-[2-(acetyloxy)ethyl]-9H-purin-6-yl-[1,1'-biphenyl]-3-carboxamide,
9-(2-hydroxyethyl)-9H-purin-6-yl-[1,1'-biphenyl]-3-carboxamide,
ethyl 2-[(1,1'-biphenyl)-3-carbonylamino-9H-purin-6-yl]acetate,
2-[(1,1'-biphenyl)-3-carbonylamino-9H-purin-6-yl]acetic acid,
diethyl [(1,1'-biphenyl)-3-carbonylamino-9H-purin-6-yl]methylphosphonate,
[(1,1'-biphenyl)-3-carbonylamino-9H-purin-6-yl]methylphosphonic acid,
9H-purin-6-ylnaphthalene-1-carboxamide,
9H-purin-6-ylnaphthalene-2-carboxamide,
(naphthalene-1-carbonylamino-9H-purin-6-yl)methylphosphonic acid,
(naphthalene-2-carbonylamino-9H-purin-6-yl)methylphosphonic acid,
9H-purin-6-yl-[1,1'-biphenyl]-4-sulfonamide, and mixtures thereof.

13. The method of claim 6, wherein said composition is administered simultaneously, separately or sequentially with administration of an additional therapy.

14. The method of claim 6, wherein the cancer is:
solid tumors, or
acute hemopathies, chronic myeloproliferative syndromes or chronic lymphoproliferative syndromes, chronic lymphoid leukemia, hairy cell lymphoma or multiple myeloma.

* * * * *